United States Patent
Loisel

(10) Patent No.: US 10,716,590 B2
(45) Date of Patent: Jul. 21, 2020

(54) METHODS AND APPARATUS FOR REMOVAL OF INTRACRANIAL HEMORRHAGE

(71) Applicant: Penumbra, Inc., Alameda, CA (US)

(72) Inventor: Steven Loisel, Castro Valley, CA (US)

(73) Assignee: Penumbra, Inc., Alameda, CA (US)

( * ) Notice: Subject to any disclaimer, the term of this patent is extended or adjusted under 35 U.S.C. 154(b) by 99 days.

(21) Appl. No.: 15/926,357

(22) Filed: Mar. 20, 2018

(65) Prior Publication Data

US 2018/0263646 A1    Sep. 20, 2018

Related U.S. Application Data

(60) Provisional application No. 62/473,779, filed on Mar. 20, 2017.

(51) Int. Cl.
| | |
|---|---|
| *A61B 17/32* | (2006.01) |
| *A61B 17/16* | (2006.01) |
| *A61B 17/00* | (2006.01) |
| *A61B 17/22* | (2006.01) |

(52) U.S. Cl.
CPC .. *A61B 17/32002* (2013.01); *A61B 17/00234* (2013.01); *A61B 17/1695* (2013.01); *A61B 17/2202* (2013.01); *A61B 2017/00685* (2013.01); *A61B 2017/32007* (2017.08); *A61B 2017/320024* (2013.01); *A61B 2017/320028* (2013.01); *A61B 2017/320032* (2013.01); *A61B 2217/005* (2013.01)

(58) Field of Classification Search
CPC ........ A61B 17/32002; A61B 17/00234; A61B 17/1695; A61B 17/2202; A61B 2017/32007; A61B 2017/00685; A61B 2017/320024; A61B 2017/320028; A61B 2017/320032; A61B 2217/005
See application file for complete search history.

(56) References Cited

U.S. PATENT DOCUMENTS

| | | | |
|---|---|---|---|
| 7,172,610 B2 | 2/2007 | Heitzmann et al. | |
| 8,114,106 B2 | 2/2012 | Straub | |
| 8,246,752 B2 | 8/2012 | Boyle, Jr. | |
| 8,366,620 B2 | 2/2013 | Nita | |
| 8,764,779 B2 | 7/2014 | Levine et al. | |
| 9,017,294 B2 | 4/2015 | McGuckin, Jr. et al. | |
| 9,055,964 B2 | 6/2015 | Cartier et al. | |
| 9,282,992 B2 | 3/2016 | Levine et al. | |
| 2009/0124975 A1* | 5/2009 | Oliver .............. | A61B 17/32002 604/119 |

(Continued)

OTHER PUBLICATIONS

Apollo System: A minimally invasive procedure for deep hemorrhage evacuation. Penumbra 2015. 4 Pages.

(Continued)

*Primary Examiner* — Erich G Herbermann
(74) *Attorney, Agent, or Firm* — Wilson Sonsini Goodrich & Rosati

(57) ABSTRACT

A system for intracranial access that includes a support assembly is described. The system includes a tubular probe shaft that may be advanced through a hole in the patient's skull. The tubular probe shaft houses a rotating element that cuts clot, and is connected to a vacuum source to aspirate clot fragments and blood from the site. The rotating element may have a bident shape.

9 Claims, 6 Drawing Sheets

(56) References Cited

U.S. PATENT DOCUMENTS

2011/0196400 A1* 8/2011 Robertson ........ A61B 17/22004
606/169
2012/0330196 A1 12/2012 Nita
2018/0008463 A1* 1/2018 Charles ............... A61F 9/00763

OTHER PUBLICATIONS

Apollo System Operations, Maintenance and service manual. Apollo system setup. Penumbra, Inc. 2014-2016. 2 pages.
"International Search Report and Written Opinion dated May 31, 2018 for International PCT Patent Application No. PCT/US18/23348".

* cited by examiner

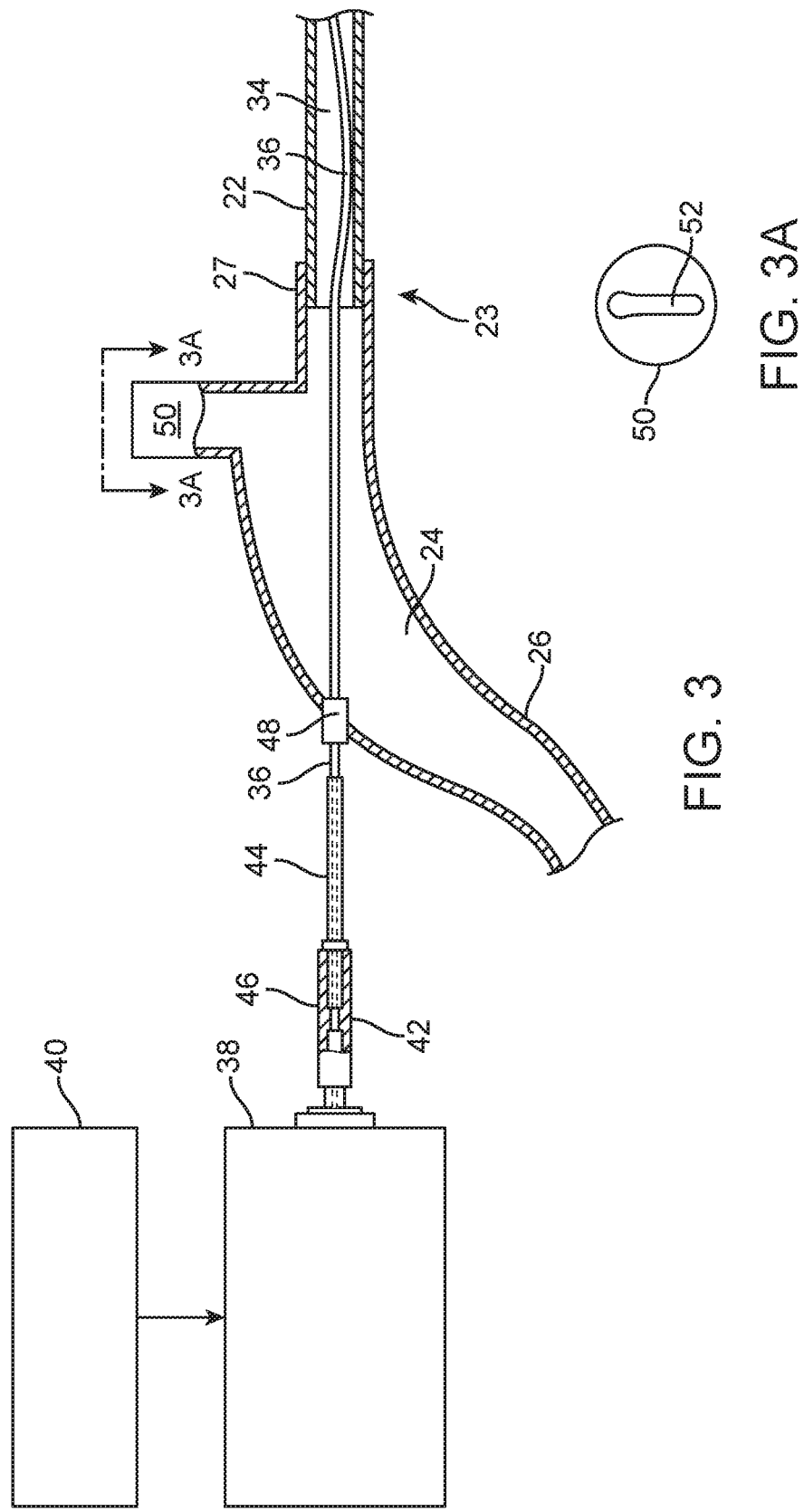

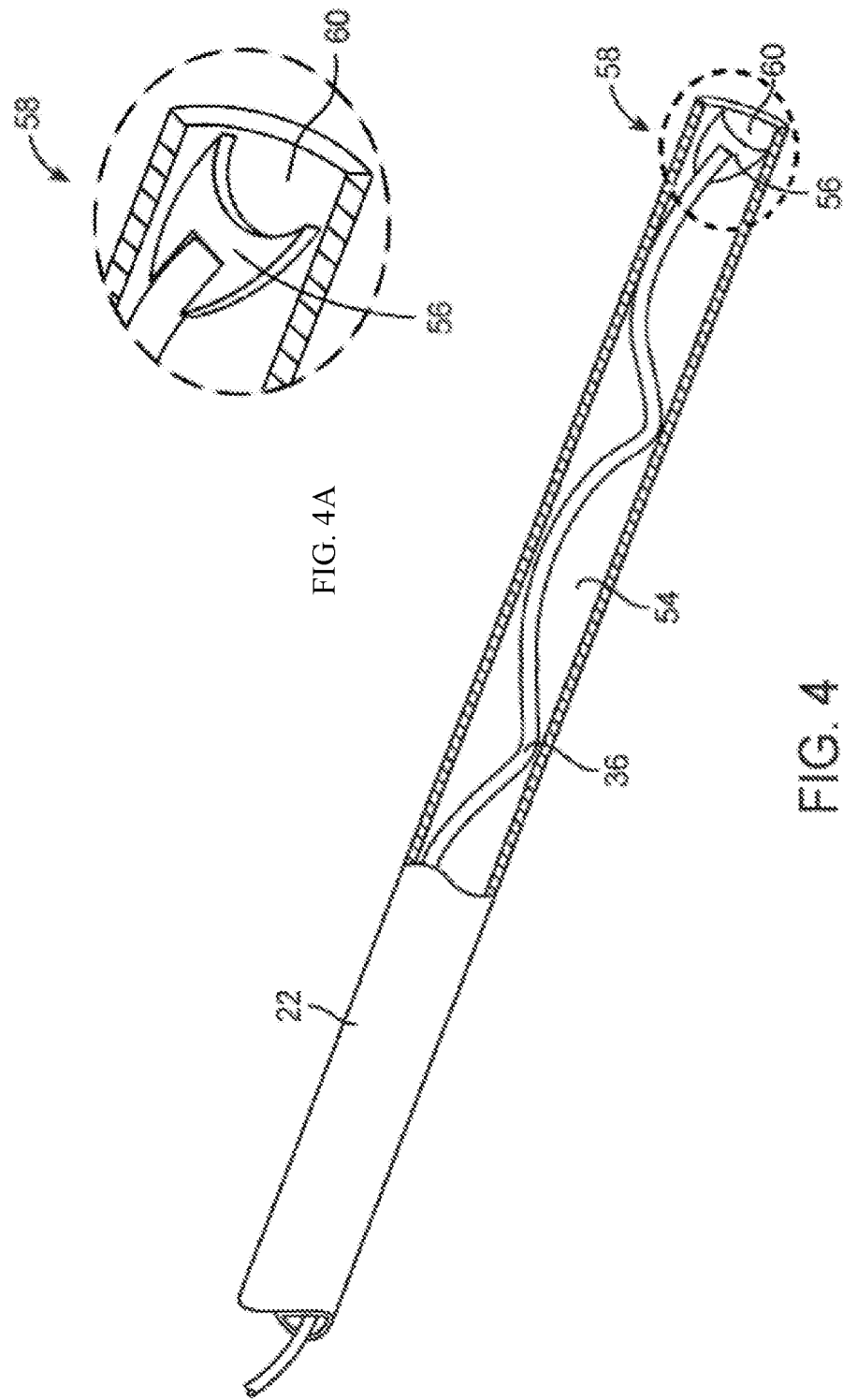

METHODS AND APPARATUS FOR REMOVAL OF INTRACRANIAL HEMORRHAGE

CROSS-REFERENCE TO RELATED APPLICATIONS

This application claims the benefit of U.S. Provisional No. 62/473,779, filed Mar. 20, 2017, the entire content of which is incorporated herein by reference.

BACKGROUND OF THE INVENTION

1. Field of the Invention

The present invention relates generally to the field of medical devices and methods. More specifically, the invention described herein relates to devices and methods for the minimally invasive removal of intracranial hemorrhages.

Stroke is a significant cause of disability and death, and a growing problem for global healthcare. More than 700,000 people in the United States alone suffer a stroke each year, and of these, more than 150,000 people die. Of those who survive a stroke, roughly 90% will suffer long term impairment of movement, sensation, memory, or reasoning, ranging from mild to severe. The total cost to the U.S. healthcare system is estimated to be over $50 billion per year.

Stroke may be caused by a blockage in a cerebral artery resulting from a thromboembolism (referred to as an "ischemic stroke"), or by a rupture of a cerebral artery (referred to as a "hemorrhagic stroke"). Hemorrhagic stroke results in bleeding within the skull, limiting blood supply to brain cells, and placing harmful pressure on delicate brain tissue. Blood loss, swelling, herniation of brain tissue, and pooling of blood that results in formation of clot mass inside the skull all rapidly destroy brain tissue. Hemorrhagic stroke is a life-threatening medical emergency with limited treatment options.

Of particular interest to the present invention, the Apollo™ System treats clots caused by hemorrhagic stroke by the administration of high frequency, low intensity ultrasound, referred to as trans-cranial Doppler (TCD) ultrasound, using a wand introduced through a burr hole in the skull. The ultrasound therapy disrupts clots to immediately reduce the deleterious pressure exerted on brain tissue. Combined with visualization and aspiration, the therapy has been shown to safely treat hemorrhagic stroke. Other cerebral disorders may also benefit from the administration of high-frequency, low intensity ultrasound, or TCD. Examples include dementia, head trauma, intracranial hematoma, Alzheimer's, and other abnormalities.

Although very effective, the use of TCD ultrasound for treating dense clot resulting from hemorrhagic stroke, or other diseased tissue, suffers from certain shortcomings. For example, the transmission of energy from an ultrasound generator to the tip of a wand results in a diminution of energy at the tip of the wand. Consequently, the amount of energy available at the tip of the wand may not be sufficient for treatment of conditions such as fibroids, tumors, cysts, or other relatively dense tissue.

Therefore, it would be desirable to provide improved apparatus and methods for the minimally invasive disruption and removal of clot in patients who have suffered hemorrhagic stroke. It would be particularly desirable if such improved apparatus and methods were also useful for treating dementia, head trauma, intracranial hematoma, Alzheimer's, and other abnormalities. At least some of these objectives will be met by the inventions described herein below.

2. Description of the Background Art

The Apollo™ System is at in the Apollo System Instructions for Use. U.S. Pat. No. 8,366,620 and US 2012/0330196 describe the use of TCD for removing hemorrhagic clot. Mechanical thrombectomy and atherectomy devices are described in U.S. Pat. Nos. 9,055,964; 9,017,294; 8,764,779; 8,246,752; 8,114,106; 7,172,610; and 9,282,992.

SUMMARY OF THE INVENTION

The present invention provides improved apparatus and methods for the minimally invasive disruption and removal of tissue lesions and clot from tissue in patients. While the methods and apparatus will be particularly useful for the removal of a clot resulting from intracranial hemorrhage in a patient's brain, it will also be useful for removal of lesions from other parts of the anatomy. The apparatus and tools of the present invention will also be useful for performing other procedures, such as removing excess fluids, tumor biopsy, tumor evacuation, and other endoscopic procedures.

In a first aspect, the present invention comprises methods for removing a lesion from a patient's brain. The method comprises advancing a distal end of a tubular probe shaft through the patient's skull to a site of the lesion. An element at the distal end of the probe shaft is actuated to cut or abrade the lesion which results in the production of lesion fragments. The lesion fragments are aspirated from the site through the tubular probe shaft.

In exemplary embodiments, the methods comprise actuating a blade to cut or abrade the lesion, typically by rotating or rotationally oscillating the blade. The blade is typically a planar blade having a central axis which is aligned with a longitudinal access of the tubular probe shaft. In specific embodiments, the blade has a "bident" or "cornu" configuration. In general, such a "bident" or "cornu" configuration has a leading distal cutting edge which is generally transverse to the axis and a base end opposite to the distal cutting edge. A pair of lateral sides may generally be tapered in a direction from distal cutting edge toward the base end. The base end will be configured to be fixedly or removably attached to a distal end of a helical or other drive shaft (as described below). The leading cutting edge will have cutting points at its lateral extremities and usually have a concave or otherwise recessed region between the lateral extremities.

The exemplary blades of the present invention are typically attached to a drive shaft or wire, more typically to a helical drive shaft or wire which is disposed in a lumen of the tubular probe shaft. The helical or other drive shaft is then rotated or rotationally oscillated to in turn rotate or rotationally oscillate the blade in order to cut or abrade the lesion.

In other specific aspects, the helical or other drive shaft or wire of the present invention is driven by a motor which is attached to a proximal end of the drive shaft. In most instances, the motor is located in a handle which is attached to a proximal end of the tubular probe shaft. The tubular probe shaft has at least one lumen running its entire length, and a vacuum may be drawn on a proximal end of the lumen in the tubular probe shaft in order to evacuate clot or other lesion fragments. In specific embodiments, the vacuum is drawn through an aspiration tube which is attached to a proximal end of the tubular drive shaft and in fluid communication with the lumen therein. The proximal end of the aspiration tube in turn, may be connected to a suitable vacuum source, and the vacuum source will typically be connected to a collection canister or other receptacle for the lesion fragments. The helical drive shaft can act as an "Archimedes screw" when it rotates in order to help "pump" fluid and entrained lesion fragments proximally through the tubular probe shaft lumen and inhibit clogging. The helical wire maintains contact with the hypotube along its length. The helix maintains contact with the hypotube for its entire length, and rotation of the helical wire within the hypotube causes continual abrading or wiping of the wire by the hypotube prevents accumulation of clot on the wire. Clot that is knocked off the wire as a result of contact with the hypotube flows towards the collection chamber. The continual process helps prevent clogging, and helps ensure continuous vacuum.

In a second aspect, the present invention comprises apparatus for removing clot or other lesion from a patient's brain. The apparatus comprises a tubular probe shaft having a lumen and a distal end configured to be advanced through a hole formed in a patient's skull. The distal end of the tubular probe shaft may be advanced to a site of the lesion, and an element at the distal end of the tubular probe shaft is configured to cut or abrade the clot to produce lesion fragments. A proximal end of the tubular shaft lumen is configured to be connected to a vacuum source to aspirate the lesion fragments from the site through the tubular probe shaft.

In specific embodiments, a helical drive shaft is disposed in the lumen of the tubular probe shaft, and the element comprises a blade configured to be rotated or rotationally oscillated by the helical drive shaft. The blade will typically be disposed at a distal opening of the lumen, where the blade is usually a planar blade aligned with a longitudinal access of the tubular probe shaft. In specific configurations, the blade will have a bident or cornu configuration, as previously discussed.

The apparatus of the present invention will usually include a handle at the proximal end of the tubular probe shaft. A motor for driving the helical or other drive shaft is typically disposed within the handle and coupled to a proximal end of the drive shaft. The motor is configured to rotate and/or rotationally oscillate the drive shaft to in turn rotate and/or rotationally oscillate the blade.

In specific embodiments, the motor and the drive shaft are axially aligned with the longitudinal access of the probe shaft. The aspiration tube, in contrast, will be offset from or diverge from the axis of the probe shaft so that the motor and probe shaft will not interfere with each other in the handle. The motor is typically battery-driven and the battery for driving the motor is typically in the handle. The aspiration tube will be connected to a proximal end of the tubular probe shaft so that the vacuum drawn through the aspiration tube will draw lesion fragments into the aspiration tube and eventually to the vacuum source and disposal canister. The helical drive shaft, in turn, ca act as an Archimedes' screw in helping move the fragments proximally through the probe shaft lumen, as previously discussed.

Aspiration control can be provided on the handle. In the exemplary embodiments, the aspiration control comprises either a slot or a generally circular aperture, or both, in the aspiration structure configured to bleed vacuum from the aspiration tube. As an example of one such embodiment, a slot, typically referred to as a Fukushima slot for aspiration control, can be manually covered by a user's thumb or finger to control the rate at which vacuum is bled from the aspiration system. By fully covering the slot, a maximum vacuum is maintained. Conversely, by fully uncovering the slot, minimum vacuum is maintained. Optionally, a switch for turning on and off and/or controlling the speed of the blade motor can be provided adjacent to or as part of the vacuum control slot. In this way, the user needs only one hand to both control the motor and to control the aspiration vacuum.

BRIEF DESCRIPTION OF THE DRAWINGS

FIG. 3 illustrates a motor drive assembly connected to a drive shaft that passes through an aspiration tube and enters a tubular probe shaft.

FIG. 3A is detailed view of a slot for controlling vacuum in the aspiration tube of FIG. taken along line 3A-3A in FIG. 3.

FIG. 4 is a detailed view of a tubular probe shaft with portions broken away to show a helical drive shaft which carries a mechanical blade.

FIG. 4A is a detailed view of the distal end of the device of FIG. 4.

DETAILED DESCRIPTION OF THE INVENTION

Some embodiments of the invention are described below. For clarity, not all features of each actual implementation are described in this specification. In the development of an actual device, some modifications may be made that result in an embodiment that still falls within the scope of the invention.

The apparatus and methods of the present invention may be used to perform any one or more of a variety of medical procedures, including removal of intracranial hematoma and other lesions, removal of excess fluid, tumor biopsy, tumor evacuation, or other endoscopic procedure. The apparatus and methods typically provide a combination of mechanical disruption, usually by cutting and/or abrading the clot or other lesion, and aspiration to remove fragments created by the mechanical disruption. The procedures most likely will be performed utilizing fluoroscopic or other imaging techniques, but such imaging techniques are not necessarily part of the present invention.

Figure 1:
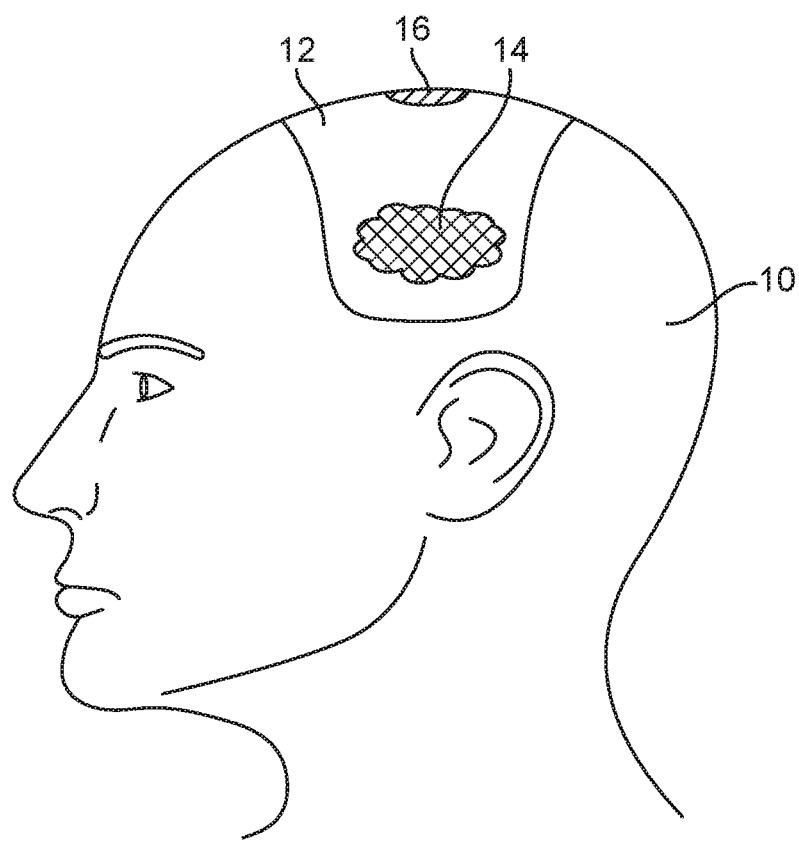
FIG. 1 is a schematic illustration of a patient's skull showing a region of clot or other lesion to be treated and a burr hole site useful for performing the methods of the present invention.

In FIG. 1, a patient's skull 10 is illustrated. Skull 10 is partly broken away to show an interior 12 which is afflicted with a lesion, mass, or region of clot 14. In a previous step in the procedure, burr hole 16 was formed on patient's skull 10, providing access from the exterior of skull 10 to the interior 12. Burr hole 16 will permit access for treatment of mass 14.

Figure 2:
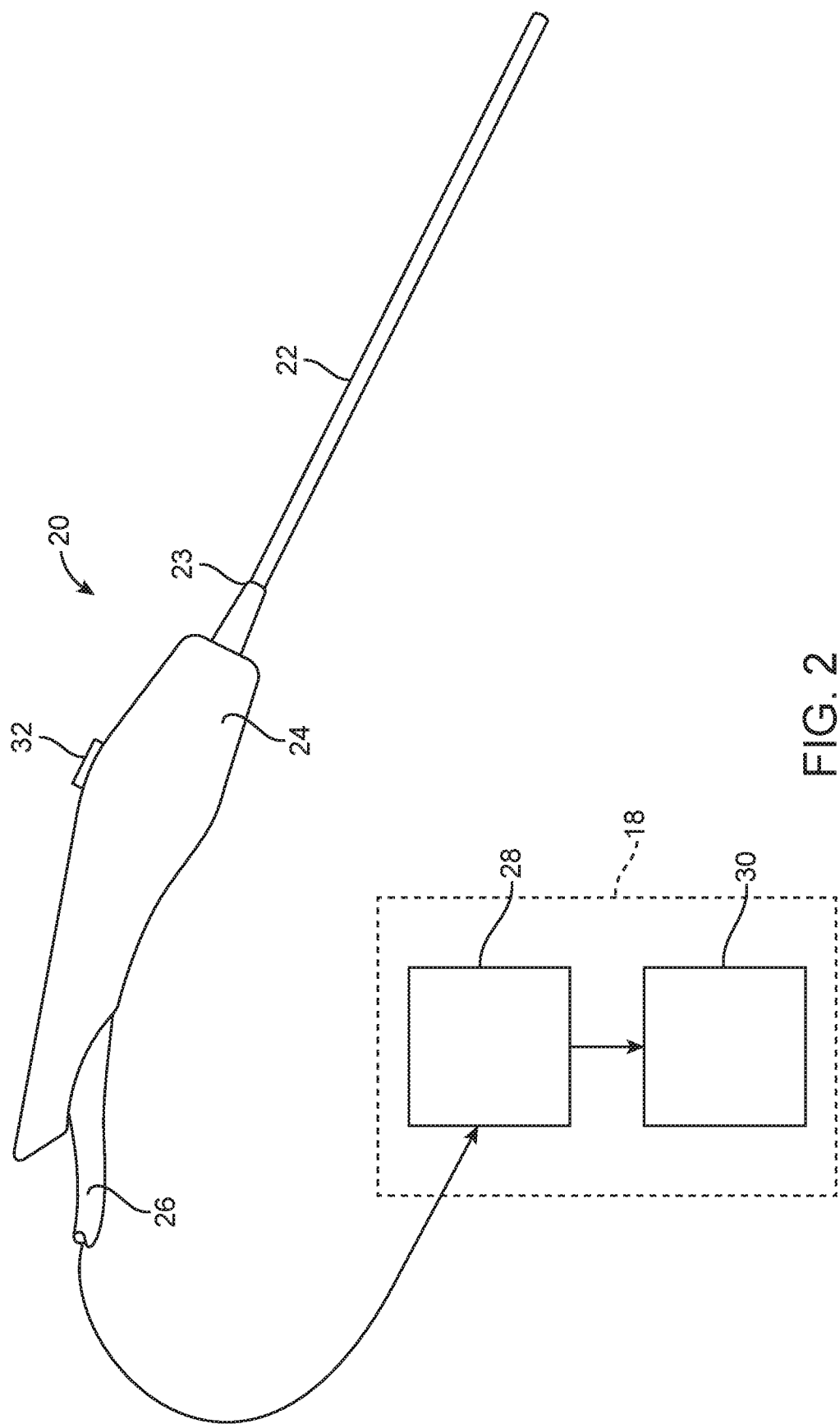
FIG. 2 illustrates a mechanical blade lesion disruption apparatus constructed in accordance with the principles of the present invention.

FIG. 2 illustrates a lesion disruption apparatus 20 constructed in accordance with the principles of the present invention. The lesion disruption apparatus 20 comprises a tubular probe shaft 22 attached at its proximal end to a handle 24. An aspiration tube 26 extends outwardly from a proximal end of the handle 24 and is attached to an external console 18 which typically includes a vacuum pump or other source 28 which aspirates and directs lesion fragments from the lesion disruption apparatus 20 to a collection canister 30. The lesion disruption apparatus 20 can be connected and disconnected from the vacuum source 28 in the external console 18, typically through a connector which is part of the aspiration tube 26 (not shown herein). In the illustrated embodiments, the lesion disruption apparatus 20 will be fully self-contained other than requiring connection to the vacuum source. That is, power for driving the abrasion/cutter will be provided by a battery within the handle, and controls for the motor to drive the cutter and for adjusting the amount of aspiration vacuum are also provided on the handle, typically by control element(s) 32.

Referring now to FIGS. 3 and 3A, a proximal end 23 of the probe shaft 22 is typically connected to a distal end 27 of the aspiration tube 26 at a location within the handle 24. A helical drive shaft 36 is disposed within a lumen 34 of the tubular probe shaft 22 and extends in a proximal direction through a distal portion of the aspiration lumen 34. A proximal end of the drive shaft 36 extends out of the aspiration tube 26 through a bushing or a bearing 48 which passes through a wall of the aspiration tube. The distal end of the drive shaft is thus exterior to the flow lumen of aspiration tube and is connected to a drive motor 38 which in turn is connected to a battery 40. In particular, the motor 38 drives a spindle 42 which is coupled to the distal end of the drive shaft 36 by a ferrule 44 and polymeric sleeve 46. The ferrule 44 is crimped or otherwise connected to the distal end of the drive shaft 36 in order to provide a larger effective diameter. The larger diameter will generally match that of the spindle 42, and the spindle and proximal end of the drive shaft may then be coupled using the polymeric sleeve 46 which bridges the ends of both the spindle 42 and the ferrule 44. Usually, a space will be left between the adjacent ends of the drive shaft and the spindle to provide for electrical isolation. The hypotube and aspiration tubing are typically separated by an aspiration chamber assembly (not illustrate in FIG. 3). This assembly acts as a junction that connects the aspiration button, aspiration tubing, and hypotube. In addition it has a very tight pass through that all the motor wire to rotate, but still creates an air tight seal.

Vacuum control within the aspiration tube 26 can be provided by an open slot 52 (FIG. 3A) formed in a branch 50 of the aspiration tube. The branch 50 will extend out of the handle, generally at the control element region 32 as illustrated in FIG. 2. The user may then manually cover the slot in order to adjust the amount of vacuum leakage through the slot. That is, when the slot is fully uncovered, the vacuum will be minimal as unimpeded air can enter through the slot 52. Conversely, by manually covering all or a portion of the slot, the degree of the vacuum can be controlled from minimum to maximum. In the alternative, a push button or other switch may be used to control aspiration.

Figure 3B:
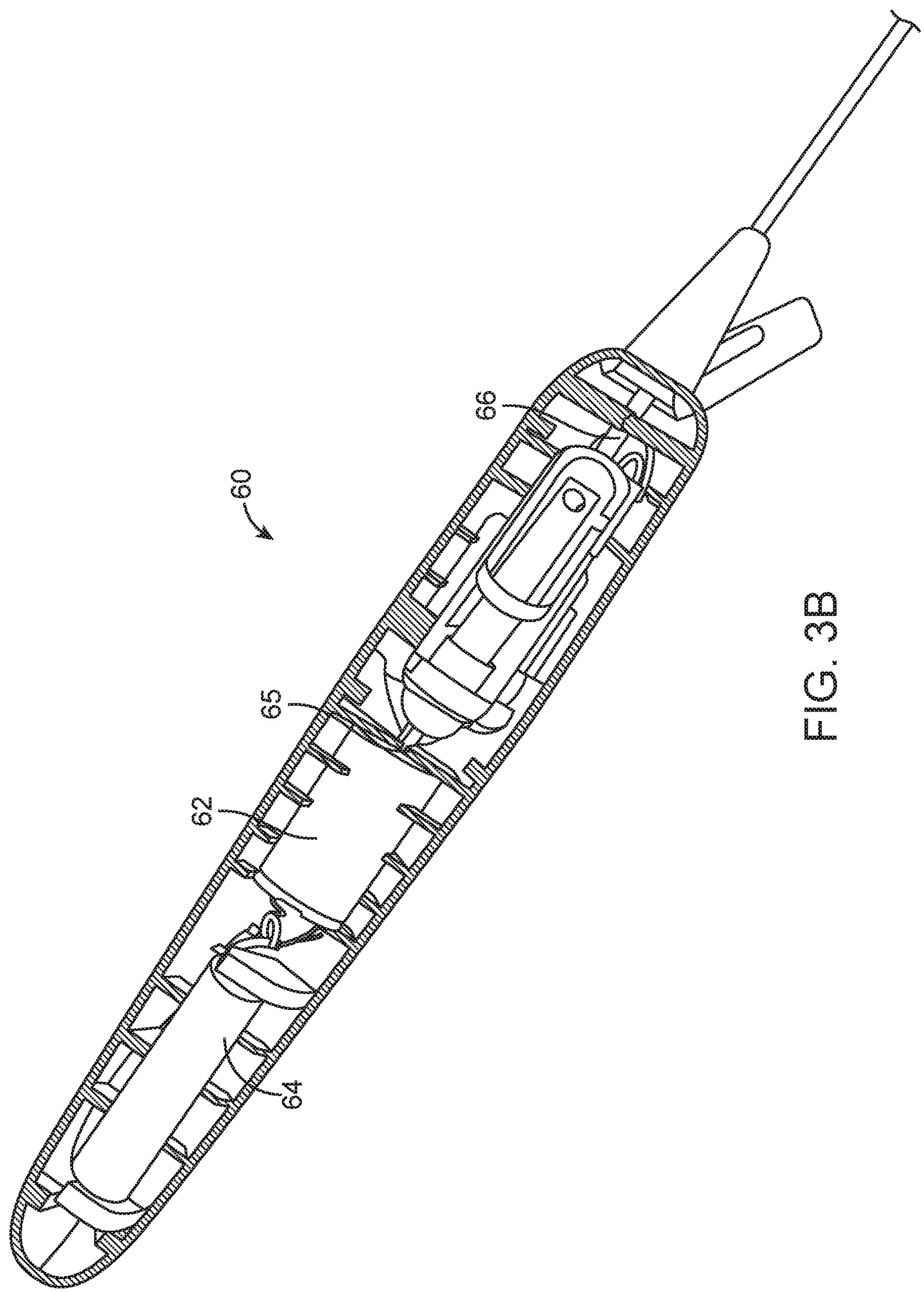
FIG. 3B illustrates the internal components of an alternative embodiment of a motor drive assembly.

FIG. 3B illustrates an exemplary alternative embodiment of a handle 60 with one side removed having a drive motor 62 and battery 64 housed therein. Battery 64 provides power to drive motor 62. Drive motor 62 drives a spindle 65 which is coupled to the distal end of a shaft, or motor wire (not visible) and functions to rotate the shaft or motor wire. The shaft, or motor wire, which is not visible in FIG. 3B, is housed within hypotube 66. When actuated by a user, motor wire (not visible) rotates within hypotube 66, and functions in a fashion similar to the embodiments described above in order to disrupt clot or other diseased tissue, and prevent clogging of the aspiration tubing.

Referring now to FIGS. 4 and 4A, the helical drive shaft 36 extends through a central lumen 54 of the tubular prove shaft 22 and carries a planar blade 56 at its distal end. The planar blade 56, in turn, is exposed in an open distal end 60 of the tube 22 so that the blade can engage and fragment a lesion as the drive shaft 36 is rotate or rotationally oscillated by motor 38. In this way, advancing the tubular probe shaft 22 into target tissue, such as a region of clot within a patient's brain, can engage the blade against the tissue in order to fragment the lesion, clot, or other anatomy present in the tissue. Perspective 58 is duplicated and enlarged to illustrate in greater detail the planar blade 56.

Figure 5:
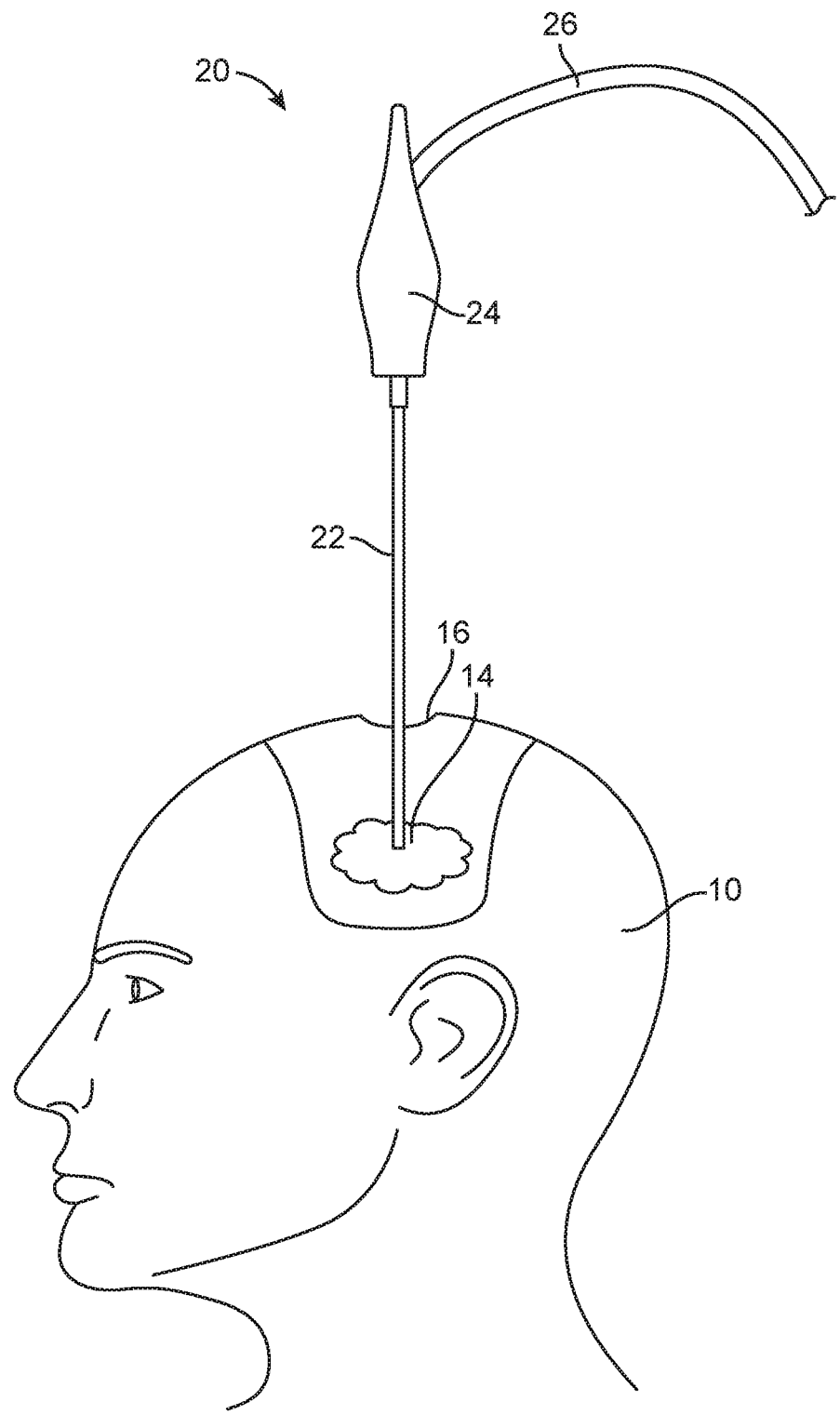
FIG. 5 illustrates use of the apparatus of FIG. 2 in removing a clot lesion from a patient's brain in accordance with the principles of the present invention.

As shown in FIG. 5, the region of intracranial clot 14 can be removed from a patient's brain by advancing the distal end of the tubular probe shaft 22 through the burr hole 16 in the patient's skull. The depth of the distal tip of the shaft can be observed, typically via indicators on the shaft or other introducer device, and the position of the tip further observed, for example, via endoscopic camera visualization, and when in the proper position, the blade can be actuated and the vacuum modulated in order to fragment and remove clot or other lesion fragments in order to treat the patient. Presence of the helical drive shaft 36 in the lumen 54 can help transport the clot fragments through the shaft and to the aspirations tube 26 from where they can be removed by the vacuum source 28 (FIG. 1).

The foregoing examples are not intended to limit the scope of the invention. All modifications, equivalents and alternatives are within the scope of the invention.

What is claimed is:

1. A method for removing a lesion from a brain of a patient, said method comprising:
   advancing a distal end of a tubular probe shaft through a skull of the patient to a site of the lesion;
   actuating a planar blade at the distal end of the tubular probe shaft to cut or abrade the lesion to produce lesion fragments, wherein the planar blade has a distal cutting edge and a pair of lateral sides that taper from the distal cutting edge to a base of the planar blade; and
   aspirating the lesion fragments from the site through the tubular probe shaft.

2. The method of claim 1, wherein the actuating comprises rotating or rotationally oscillating the planar blade.

3. The method of claim 2, wherein the planar blade is aligned with a longitudinal axis of the tubular probe shaft.

4. The method of claim 3, wherein the planar blade has a bident configuration and the distal cutting edge comprises a concaved region between two cutting edges at lateral extremities, wherein the pair of lateral sides taper from the two cutting edges to the base of the planar blade.

5. The method of claim 2, wherein the planar blade is attached to a helical drive shaft disposed in a lumen of the tubular probe shaft and rotating or rotationally oscillating the planar blade comprises rotating or rotationally oscillating the helical drive shaft.

6. The method of claim 5, wherein rotating or rotationally oscillating the helical drive shaft comprises driving a proximal end of the helical drive shaft with a motor.

7. The method of claim 6, wherein the motor is located in a handle attached to a proximal end of the tubular probe shaft.

8. The method of claim 7, wherein aspirating comprises drawing a partial vacuum on an aspiration tube attached to the proximal end of the tubular probe shaft, wherein a lumen of the aspiration tube is contiguous with the lumen of the tubular probe shaft.

9. The method of claim 8, wherein the motor and the helical drive shaft are axially aligned with the tubular probe shaft and the aspiration tube diverges from the longitudinal axis of the tubular probe shaft.

\* \* \* \* \*